United States Patent [19]
Ulrich

[11] Patent Number: 5,925,642
[45] Date of Patent: Jul. 20, 1999

[54] PYRIDOPYRIMIDINES

[75] Inventor: Wolf-Rüdiger Ulrich, Constance, Germany

[73] Assignee: Byk Gulden Lomberg Chemische Fabrik GmbH, Constance, Germany

[21] Appl. No.: 09/068,936

[22] PCT Filed: Nov. 16, 1996

[86] PCT No.: PCT/EP96/05046

§ 371 Date: May 21, 1998

§ 102(e) Date: May 21, 1998

[87] PCT Pub. No.: WO97/19946

PCT Pub. Date: Jun. 5, 1997

[30] Foreign Application Priority Data

Nov. 24, 1995 [CH] Switzerland ............... 3322/95

[51] Int. Cl.⁶ ............... A61K 31/505; C07D 487/04
[52] U.S. Cl. ............... 514/258; 544/58.7; 544/117; 544/279; 514/228.5; 514/234.2
[58] Field of Search ............... 544/117, 279, 544/58.7; 514/258, 234.2, 228.5

[56] References Cited

FOREIGN PATENT DOCUMENTS

WO 94/14809  7/1994  WIPO.

*Primary Examiner*—Bernard Dentz
*Attorney, Agent, or Firm*—Jacobson, Price, Holman & Stern, PLLC

[57] ABSTRACT

The invention concerns compounds of formula (I) in which the substituents and symbols have the meanings given in the specification. These compounds are advantageous as resistance modulators.

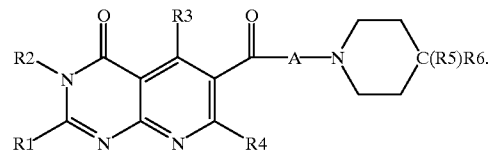

9 Claims, No Drawings

PYRIDOPYRIMIDINES

This application is a 371 PCT/EP96/05046 filed Nov. 16, 1996.

FIELD OF APPLICATION OF THE INVENTION

The invention relates to novel pyridopyrimidine derivatives which are used in the pharmaceutical industry for the production of medicaments.

1. Prior Art

The U.S. Pat. Application WO 94/14809 describes fused uracil derivatives which act as resistance modulators.

2. Description of the Invention

It has now been found that the pyridopyrimidines which are described below in greater detail and which differ from the published compounds, in particular by the substitution in the pyrimidine ring, have surprising and particularly advantageous properties.

The invention relates to compounds of the formula I (see attached formula sheet) in which $R1$ is hydrogen or 1–7C-alkyl, $R2$ is 1–7C-alkyl, phenyl, phenyl-1–4C-alkyl, Ar-1–4C-alkyl, Ar or 1–7C-alkylene substituted by —N(R7)R8, where Ar is phenyl substituted by R9, R10 and R11, $R3$ is phenyl or phenyl substituted by R31 and R32, where
$R31$ is hydrogen, hydroxyl, halogen, nitro, cyano, carboxyl, trifluoromethyl, 1–4C-alkyl, 1–4C-alkoxy, completely or partly fluorine-substituted 1–4C-alkoxy, 1–4C-alkoxycarbonyl, 1–4C-alkylcarbonyl, amino or mono- or di-1–4C-alkylamino and
$R32$ is hydrogen, hydroxyl, halogen, nitro, trifluoromethyl, 1–4C-alkyl or 1–4C-alkoxy, $R4$ is 1–4C-alkyl, A is 1–20C-alkylene or the group A1-X-A2, in which
A1 is 1–17C-alkylene,
X is O (oxygen) and
A2 is 2–18C-alkylene, where the total of the alkylene carbon atoms of A1 and A2 is not greater than 19, $R5$ is Ar1 and $R6$ is Ar2, or in which $R5$ and $R6$ together are methylene substituted by Ar1 and Ar2 [=C(Ar1)Ar2], or in which $R5$ is hydrogen and $R6$ is methyl substituted by Ar1 and Ar2 [—CH(Ar1)Ar2] or hydroxymethyl substituted by Ar1 and Ar2 [—C(OH)(Ar1)Ar2], where
Ar1 is phenyl or phenyl substituted by one or two identical or different substituents from the group consisting of hydroxyl, halogen, nitro, trifluoromethyl, 1–4C-alkyl and 1–4C-alkoxy and
Ar2 is phenyl or phenyl substituted by one or two identical or different substituents from the group consisting of hydroxyl, halogen, 1–4C-alkyl and 1–4C-alkoxy, $R7$ is 1–7C-alkyl, 3–8C-cycloalkyl, phenyl-1–4C-alkyl or Ar-1–4C-alkyl and $R8$ is 1–7C-alkyl, 3–8C-cycloalkyl, phenyl-1–4C-alkyl or Ar-1–4C-alkyl, where
Ar is phenyl substituted by R9, R10 and R11,
or in which $R7$ and $R8$, together and including the nitrogen atom to which both are bonded, are an unsubstituted or substituted heterocycle which is selected from the group consisting of pyrrolidine, piperidine, piperazine, morpholine, thiomorpholine, indoline, octahydro-1H-indole, 1,2,3,4-tetrahydroquinoline, 1,2,3,4-tetrahydroisoquinoline, decahydroquinoline and decahydroisoquinoline, where a substituted pyrrolidino radical is substituted by one or two identical or different substituents selected from the group consisting of 1–4C-alkyl, 1–4C-alkoxy, 1–4C-alkoxy-1–4C-alkyl, 1–4C-alkoxycarbonyl, 1–4C-alkylcarbonyloxy, hydroxy-1–4C-alkyl, hydroxyl and carboxyl, a substituted piperidino radical is substituted by one, two or three identical or different substituents selected from the group consisting of 1–4C-alkyl, gem-di-1–4C-alkyl, 1–4C-alkoxy, 1–4C-alkoxy-1–4C-alkyl, 1–4C-alkoxycarbonyl, 1–4C-alkylcarbonyl, 1–4C-alkylcarbonyl-1–4C-alkyl, hydroxy-1–4C-alkyl, dihydroxy-1–4C-alkyl, di-1–4C-alkylamino, di-1–4C-alkylamino-1–4C-alkyl, pyrrolidino, piperidino, pyrrolidinyl-1–4C-alkyl, piperidinyl-1–4C-alkyl, carbamoyl, di-1–4C-alkylaminocarbonyl, piperidinocarbonyl, morpholinocarbonyl, phenyl, phenyl substituted by R9, R10 and R11, phenyl-1–4C-alkyl, benzoyl, benzoyl substituted by halogen, formyl, carboxyl, cyano, hydroxyl, halogen and sulfo, a substituted piperazino radical in the 2-, 3-, 5- or 6-position can be substituted by a 1–4C-alkyl radical and in the 4-position is substituted by a substituent selected from the group consisting of 1–4C-alkyl, 3–7C-cycloalkyl, 3–7C-cycloalkyl-1–4C-alkyl, 1–4C-alkoxycarbonyl, 1–4C-alkoxycarbonyl-1–4C-alkyl, hydroxy-1–4C-alkyl, di-1–4C-alkylamino-1–4C-alkyl, halo-1–4C-alkyl, carbamoyl, phenyl, phenyl substituted by R9, R10 and R11, phenyl-1–4C-alkyl, phenyl-1–4C-alkyl substituted in the phenyl radical by R9, R10 and R11, naphthyl, benzhydryl and benzhydryl substituted by halogen, a substituted morpholino radical is substituted by one or two identical or different 1–4C-alkyl radicals, a substituted indolin-1-yl radical in the 2- and/or 3-position can be substituted by a carboxyl group or by one or two identical or different 1–4C-alkyl radicals, and can be substituted in the benzo moiety by one or two identical or different substituents selected from the group consisting of 1–4C-alkyl, halogen and nitro, a substituted 1,2,3,4-tetrahydroquinoline radical is substituted by one or two identical or different substituents selected from the group consisting of 1–4C-alkyl, 1–4C-alkoxycarbonyl and halogen, a substituted 1,2,3,4-tetrahydroisoquinoline radical can be substituted in the positions 1, 3 and/or 4 by one or two identical or different substituents selected from the group consisting of 1–4C-alkyl, carboxyl, phenyl, phenyl substituted by R9, R10 and R11, phenyl-1–4C-alkyl and phenyl-1–4C-alkyl substituted in the phenyl radical by R9, R10 and R11, and can be substituted in the benzo moiety by one or two substituents selected from the group consisting of hydroxyl, 1–4C-alkoxy and di-1–4C-alkylamino, and where $R9$ is hydrogen, hydroxyl, 1–4C-alkyl, 1–4C-alkoxy, 1–4C-alkylcarbonyl, halogen, 1–4C-alkylamino or nitro, $R10$ is hydrogen, hydroxyl, 1–4C-alkyl, 1–4C-alkoxy, halogen or nitro and R11 is hydrogen or trifluoromethyl,
and their salts.

1–7C-Alkyl represents straight-chain or branched alkyl radicals having 1 to 7 carbon atoms. Examples which may be mentioned are the heptyl radical, hexyl radical, neopentyl radical, isopentyl radical, pentyl radical, butyl radical, isobutyl radical, sec-butyl radical, tert-butyl radical, propyl radical, isopropyl radical, ethyl radical and the methyl radical.

Ar-1–4C-alkyl represents one of the 1–4C-alkyl radicals substituted by Ar mentioned below where Ar is phenyl substituted by R9, R10 and R11. Examples which may be mentioned are the 4-methoxybenzyl radical, the 3,4-dimethoxybenzyl radical, the 3,4-dihydroxybenzyl radical, the 2-(2-trifluoromethylphenyl)ethyl radical and the 3-hydroxy-4-methoxybenzyl radical.

Phenyl-1–4C-alkyl represents one of the 1–4C-alkyl radicals substituted by phenyl mentioned below. Examples which may be mentioned are the phenethyl radical and the benzyl radical.

1–7C-Alkylene represents straight-chain or branched 1–7C-alkylene radicals, for example the methylene radical (—CH$_2$—), ethylene radical (—CH$_2$—CH$_2$—), trimethylene radical (—CH$_2$—CH$_2$—CH$_2$—), tetramethylene radical (—CH$_2$—CH$_2$—CH$_2$—CH$_2$—), 1,2-dimethylethylene radical [—CH(CH$_3$)—CH(CH$_3$)—], 1,1-dimethylethylene radical [—C(CH$_3$)$_2$—CH$_2$—], 2,2,-dimethylethylene radical [—CH$_2$—C(CH$_3$)$_2$—], isopropylidene radical [—C(CH$_3$)$_2$—], 1-methylethylene radical [—CH(CH$_3$)—CH$_2$—], pentamethylene radical (—CH$_2$—CH$_2$—CH$_2$—CH$_2$—CH$_2$—), hexamethylene radical (—CH$_2$—CH$_2$—CH$_2$—CH$_2$—CH$_2$—CH$_2$—) and the heptamethylene radical (—CH$_2$—CH$_2$—CH$_2$—CH$_2$—CH$_2$—CH$_2$—).

Halogen within the meaning of the present invention is bromine, chlorine and fluorine.

1–4C-Alkyl represents straight-chain or branched alkyl radicals having 1 to 4 carbon atoms. Examples which may be mentioned are the butyl radical, isobutyl radical, sec-butyl radical, tert-butyl radical, propyl radical, isopropyl radical, ethyl radical and the methyl radical.

1–4C-Alkoxy represents a radical which, in addition to the oxygen atom, contains one of the abovementioned 1–4C-alkyl radicals. Examples which may be mentioned are the methoxy radical and the ethoxy radical.

1–4C-Alkoxy completely or partly substituted by fluorine which may be mentioned are, for example, the 1,2,2-trifluoroethoxy radical, the 2,2,3,3,3-pentafluoropropoxy radical, the perfluoroethoxy radical and in particular the 1,1,2,2-tetrafluoroethoxy radical, the trifluoromethoxy radical, the 2,2,2-trifluoroethoxy radical and the difluoromethoxy radical.

1–4C-Alkoxycarbonyl represents a radical which, in addition to the carbonyl group, contains one of the abovementioned 1–4C-alkoxy radicals. Examples which may be mentioned are the methoxycarbonyl radical and the ethoxycarbonyl radical.

1–4C-Alkylcarbonyl represents a radical which, in addition to the carbonyl group, contains one of the abovementioned 1–4C-alkyl radicals. An example which may be mentioned is the acetyl radical.

Mono- and di-1–4C-alkylamino contain, in addition to the nitrogen atom, one or two of the abovementioned 1–4C-alkyl radicals. Di-1–4C-alkylamino is preferred, and in this case in particular dimethyl-, diethyl- or diisopropylamino.

1–20C-Alkylene represents straight-chain or branched alkylene radicals having 1 to 20 carbon atoms. Examples which may be mentioned are the radicals ethylene (—CH$_2$—CH$_2$—), trimethylene (—CH$_2$—CH$_2$—CH$_2$—), tetramethylene (—CH$_2$—CH$_2$—CH$_2$—CH$_2$—), pentamethylene (—CH$_2$—CH$_2$—CH$_2$—CH$_2$—CH$_2$13 ), hexamethylene(—CH$_2$(CH$_2$)$_4$—CH$_2$—), heptamethylene (—CH$_2$—(CH$_2$)$_5$—CH$_2$—), octamethylene (—CH$_2$—(CH$_2$)$_6$—CH$_2$—), decamethylene (—CH$_2$—(CH$_2$)$_8$—CH$_2$—), dodecamethylene (—CH$_2$—(CH$_2$)$_{10}$—CH$_2$—), hexadecamethylene (—CH$_2$—(CH$_2$)$_{14}$—CH$_2$—), octadecamethylene (—CH$_2$—(CH$_2$)$_{16}$—CH$_2$—), 1,2-dimethylethylene [—CH(CH$_3$)—CH(CH$_3$)—], 1,1-dimethylethylene [—C(CH$_3$)$_2$—CH$_2$—], isopropylidene [—C(CH$_3$)$_2$—], 2,2-dimethylpropylene [—CH$_2$—C(CH$_3$)$_2$—CH$_2$—], 2-methylpropylene [—CH$_2$—CH(CH$_3$)—CH$_2$—] and 2-methylethylene [—CH$_2$—CH(CH$_3$)—].

1–17C-Alkylene represents straight-chain or branched alkylene radicals having 1 to 17 carbon atoms. Examples which may be mentioned are the radicals methylene (—CH$_2$—) and heptadecamethylene [—CH$_2$—(CH$_2$)$_{15}$—CH$_2$—].

2–18C-Alkylene represents straight-chain or branched alkylene radicals having 2–18 carbon atoms.

3–8C-Cycloalkyl represents the cyclopropyl, cyclobutyl, cyclopentyl, cyclohexyl, cycloheptyl and cyclooctyl radicals.

1–4C-Alkoxy-1–4C-alkyl represents one of the abovementioned 1–4C-alkyl radicals which is substituted by one of the abovementioned 1–4C-alkoxy radicals. Examples which may be mentioned are the methoxymethyl radical, the methoxyethyl radical and the butoxyethyl radical.

1–4C-Alkylcarbonyloxy represents a radical which, in addition to the carbonyloxy radical, contains one of the abovementioned 1–4C-alkyl radicals. An example which may be mentioned is the acetyloxy radical.

Hydroxy-1–4C-alkyl represents one of the abovementioned 1–4C-alkyl radicals which is substituted by hydroxyl. Examples which may be mentioned are the hydroxymethyl radical, the 2-hydroxyethyl radical or the 3-hydroxypropyl radical.

Gem-di-1–4C-alkyl represents two of the abovementioned 1–4C-alkyl radicals which are linked to an identical ring position.

1–4C-Alkylcarbonyl-4C-alkyl represents one of the abovementioned 1–4C-alkyl radicals which is substituted by one of the abovementioned alkylcarbonyl radicals. Examples which may be mentioned are the 2-oxopropyl radical (acetonyl radical) and the 2-oxobutyl radical.

Dihydroxy-1–4C-alkyl represents one of the abovementioned 1–4C-alkyl radicals which is substituted by two hydroxyl groups. An example which may be mentioned is the 1,2-dihydroxyethyl radical.

Di-1–4C-alkylamino-1–4C-alkyl represents one of the abovementioned 1–4C-alkyl radicals which is substituted by one of the abovementioned di-1–4C-alkylamino radicals. Examples which may be mentioned are the dimethylaminomethyl radical, the dimethylaminoethyl radical and the diethylaminoethyl radical.

pyrrolidinyl-1–4C-alkyl and piperidinyl-1–4C-alkyl represent the abovementioned 1–4C-alkyl radicals which are substituted by a pyrrolidinyl radical or piperidinyl radical. Examples which may be mentioned are the 2-pyrrolidinoethyl radical, the 2-piperidinoethyl radical, the piperidinomethyl radical and the 2-(4-piperidinyl)ethyl radical.

Di-1–4C-alkylaminocarbonyl represents a radical which, in addition to the carbonyl group, contains one of the abovementioned di-1–4C-alkylamino groups. Examples which may be mentioned are the dimethylcarbamoyl radical and the diethylcarbamoyl radical.

Examples of phenyl radicals substituted by R9, R10 and R11 which may be mentioned are the radicals 4-acetyl, 3,4-dimethoxy, 2-methoxy, 2-ethoxy, 3-methoxy, 4-methoxy, 4-fluoro, 4-chloro, 2-chloro, 3-chloro, 3,4-dichloro, 3-trifluoromethyl, 2-trifluoromethyl, 2-methyl, 3-methyl, 4-methyl, 2,3dimethyl, 2,4-dimethyl, 3,4-dimethyl, 2,5-dimethyl, 2-nitro, 3-nitro, 4-nitro, 2,6-dinitro-4-trifluoromethyl and 5-chloro-2-methylaminophenyl.

Phenyl-1–4C-alkyl substituted by R9, R10 and R11 in the phenyl radical represents one of the abovementioned 1–4C-alkyl radicals which is substituted by phenyl substituted by R9, R10 and R11.

Exemplary phenyl radicals substituted by R31 and R32 which may be mentioned are the radicals 2-aminophenyl, 3-aminophenyl, 2-bromophenyl, 4-bromophenyl, 4-carboxyphenyl, 2-chlorophenyl, 3-chlorophenyl, 4-chlorophenyl, 3-bromophenyl, 2,3-dichlorophenyl, 2,4-dichlorophenyl, 2-chloro-5-nitrophenyl, 4-chloro-3-nitrophenyl, 2,6-dichlorophenyl, 3-cyanophenyl, 4-cyanophenyl, 4-diethylaminophenyl, 3-fluorophenyl, 2,4-difluorophenyl, 2-fluoro-5-nitrophenyl, 3-hydroxyphenyl, 2-hydroxy-4-methoxyphenyl, 2,4-dihydroxyphenyl, 2,3-dimethoxyphenyl, 2,4-dimethoxyphenyl, 4-dimethylaminophenyl, 2-methylphenyl, 3-methylphenyl, 4-methylphenyl, 4-methyl-3-nitrophenyl, 2,4-dimethylphenyl, 2-nitrophenyl, 3-nitrophenyl, 4-nitrophenyl, 2,4-dinitrophenyl, 3,4-dinitrophenyl, 3,5-dinitrophenyl, 2,6-dinitrophenyl, 4-ethoxyphenyl, 3,5-bis (trifluoromethyl)phenyl, 3-trifluoromethylphenyl and 4-trifluoromethylphenyl.

3–7C-Cycloalkyl represents the cyclopropyl, cyclobutyl, cyclopentyl, cyclohexyl and cycloheptyl radicals.

3–7C-Cycloalkyl-1–4C-alkyl represents one of the abovementioned 1–4C-alkyl radicals which is substituted by one of the abovementioned 3–7C-cycloalkyl radicals. Examples which may be mentioned are the cyclopropylmethyl radical, the cyclohexymethyl radical and the cyclohexylethyl radical.

1–4C-Alkoxycarbonyl-1–4C-alkyl represents one of the abovementioned 1–4C-alkyl radicals which is substituted by one of the abovementioned 1–4C-alkoxycarbonyl radicals. An example which may be mentioned is the ethoxycarbonylmethyl radical.

Halo-1–4C-alkyl represents one of the abovementioned 1–4C-alkyl radicals which is substituted by one of the abovementioned halogen atoms. An example which may be mentioned is the 3-chloropropyl radical.

Substituted pyrrolidino radicals which may be mentioned are, for example, the 2-methoxymethylpyrrolidino, 2-methoxycarbonylpyrrolidino, 2-methylpyrrolidino, 2,5-dimethylpyrrolidino, 2-carboxypyrrolidino, 4-hydroxy-2-methoxycarbonylpyrrolidino, 4-hydroxy-2-ethoxycarbonylpyrrolidino, 2-(2-hydroxyethyl)pyrrolidino, 4-hydroxy-2-carboxypyrrolidino, 2-hydroxymethylpyrrolidino, 3-hydroxypyrrolidino and 4-acetoxy-2-carboxypyrrolidino radicals.

Substituted piperidino radicals which may be mentioned are, for example, the 3-hydroxypiperidino, 2-carboxypiperidino, 4-[2-(4-piperidyl)ethyl]piperidino, 4-cyano-4-phenylpiperidino, 4,4-dihydroxypiperidino, 2-n-propylpiperidino, 5-ethyl-2-methylpiperidino, 2-dimethylaminomethylpiperidino, 2-(2-pyrrolidinoethyl) piperidino, 4-benzyl-4-hydroxypiperidino, 4-formyl-4-phenylpiperidino, 4-hydroxymethyl-4-phenylpiperidino, 4-n-propylpiperidino, 4-(3-phenylpropyl)piperidino, 4-dimethylaminopiperidino, 4-ethoxy-4-phenylpiperidino, 4-hydroxy-4-(4-fluorophenyl)piperidino, 2-(1-hydroxy) benzylpiperidino, 2-(1-hydroxy)-4-chlorobenzylpiperidino, 4-(1-pyrrolidinyl)piperidino, 4,4-dimethylpiperidino, 4-phenyl-4-propyloxypiperidino, 2,6-dimethylpiperidino, 3-hydroxy-2,6-dihydroxymethylpiperidino, 2,6-di(2-oxobutyl)piperidino, 4-hydroxypiperidino, 4-hydroxy-4-phenylpropylpiperidino, 4-(1-oxopropyl)-4-phenylpiperidino, 4-(1-oxobutyl)-4-phenylpiperidino, 4-phenyl-4-propyloxycarbonylpiperidino, 4-phenyl-4-(1-piperidinylcarbonyl)piperidino, 4-carbamoyl-4-phenylpiperidino, 4-carbamoyl-4-dimethylaminopiperidino, 4-morpholinocarbonyl-4-phenylpiperidino, 4-carbamoylpiperidino, 4-[3-(4-piperidinyl)propyl] piperidino, 2-carboxy-5-hydroxypiperidino, 4-acetyl-4-phenylpiperidino, 2,ethyl-2-methylpiperidino, 4-ethoxycarbonyl-4-phenylpiperidino, 4-bromo-4-phenylpiperidino, 4-carboxy-4-phenylpiperidino, 4-hydroxy-4-(3-trifluoromethylphenyl)piperidino, 4-formylpiperidino, 4-carboxypiperidino, 4-(4-fluorobenzoyl)piperidino, 2-(1,2-dihydroxyethyl) piperidino, 2-(2-dimethylaminoethyl)piperidino, 4-(2-dimethylaminoethyl)piperidino, 4-(2-dimethylaminoethyl) piperidino, 4-(4-chlorobenzoyl)piperidino, 4-(2-butyloxyethyl)piperidino, 4-[2-(1-piperidinyl)ethyl] piperidino, 2,3-dicarboxypiperidino, 2,4-dicarboxypiperidino, 2,6-dicarboxypiperidino, 4-sulfopiperidino, 2-ethoxycarbonylpiperidino, 2-methylpiperidino, 2,2,6,6-tetramethylpiperidino, 4-hydroxy-2,2,6,6-tetramethylpiperidino, 2,6-dimethylpiperidino, 2-hydroxymethylpiperidino, 2-ethylpiperidino, 2-(2-hydroxyethyl)piperidino, 3-diethylcarbamoylpiperidino, 3-ethoxycarbonylpiperidino, 4-hydroxy-4-(4-chlorophenyl)piperidino, 4-(1-piperidinyl) piperidino and the 4-benzylpiperidino radicals.

Substituted piperazino radicals which may be mentioned, for example, are the 4-methylpiperazino, 4-[2-(2-trifluoromethylphenyl)ethyl]piperazino, 4-(3-chloropropyl) piperazino, 4-phenylpiperazino, 4-(2-methylphenyl) piperazino, 4-(2,3-dimethylphenyl)piperazino, 4-(2-chlorophenyl)piperazino, 4-(2-methoxyphenyl)piperazino, 4-(2-ethoxyphenyl)piperazino, 4-(3-chlorophenyl) piperazino, 4-(4-fluorophenyl)piperazino, 4-(4-chlorophenyl)piperazino, 4,4-methoxyphenyl)piperazino, 4-carbamoylpiperazino, 4-(3,4-dimethylphenyl)piperazino, 4-(3-hydroxypropyl)piperazino, 3-methyl-4-phenylpiperazino, 3-methyl-4-(3-chlorophenyl)piperazino, 4-benzylpiperazino, 4-propylpiperazino, 4-(3-methylphenyl)piperazino, 4-(3-methoxyphenyl)piperazino, 4-(4-methylphenyl)piperazino, 4-(2,5-dimethylphenyl) piperazino, 4-benzhydrylpiperazino, 4-cyclopropylpiperazino, 4-cyclobutylpiperazino, 4-cyclopentylpiperazino, 4-cyclohexylpiperazino, 4-cycloheptylpiperazino, 4-n-butylpiperazino, 4-isobutylpiperazino, 4-tert-butylpiperazino, 4-dimethylaminomethylpiperazino, 4-(2-diethylaminoethyl) piperazino, 4-(3-trifluoromethylphenyl)piperazino, 4-(1-phenylethyl)piperazino, 4-ethoxycarbonylmethylpiperazino, 4-(2-phenylethyl) piperazino 4-(2-cyclohexylethyl)piperazino, 4-(2-dimethylaminoethyl)piperazino, 4-(2-hydroxyphenyl) piperazino, 4-(3,4-dimethoxyphenyl)piperazino, 4-isopropylpiperazino, 3-methyl-4-(3-methoxyphenyl) piperazino, 4-(4-hydroxyphenyl)piperazino, 3-methyl-4-(3-methylphenyl)piperazino, 4-(3-hydroxyphenyl)piperazino, 4-(2,6-dinitro-4-trifluoromethylphenyl)piperazino, 4-(1-naphthyl)piperazino, 4-(2-hydroxyethyl)piperazino, 4-(4-nitrophenyl)piperazino, 4-(4-acetylphenyl)piperazino, 4-ethoxycarbonylpiperazino and the 4-(4-chlorobenzhydryl) piperazino radicals.

A substituted morpholino radical which may be mentioned is, for example, the 3,5-dimethylmorpholino radical.

Substituted indolin-1-yl radicals which may be mentioned are, for example, the 2-carboxy-1-indolinyl, 6-fluoro-1-indolinyl, 5-bromo-1-indolinyl, 2,7-dimethyl-1-indolinyl, 2-methyl-1-indolinyl, 5-bromo-7-nitro-1-indolinyl, 5-nitro-1-indolinyl, 2,3-dimethyl-1-indolinyl and the 6-nitro-1-indolinyl radicals.

Substituted 1,2,3,4-tetrahydroquinoline radicals which may be mentioned are, for example, the 2-ethoxycarbonyl-1,2,3,4-tetrahydro-1-quinolinyl, 2-methyl-1,2,3,4-tetrahydro-1-quinolinyl, 6-methyl-1,2,3,4-tetrahydro-1-quinolinyl, 6-fluoro-2-methyl-1,2,3,4-tetrahydro-1-quinolinyl, 4-methyl-1,2,3,4-tetrahydro-1-quinolinyl and the 2-fluoro-6-methyl-1,2,3,4-tetrahydro-1-quinolinyl radicals.

Substituted 1,2,3,4-tetrahydroisoquinoline radicals which may be mentioned are, for example, 1-methyl-6,7-dihydroxy-1,2,3,4-tetrahydro-2-isoquinolinyl, 3-carboxy-1,2,3,4-tetrahydro-2-isoquinolinyl, 6,7-dimethoxy-1,2,3,4-tetrahydro-2-isoquinolinyl, 1-benzyl-1,2,3,4-tetrahydro-2-isoquinolinyl, 3-tert-butyl-6-methoxy-4-phenyl-1,2,3,4-tetrahydro-2-isoquinolinyl, 1-(3,4-dimethoxybenzyl)-6,7-dimethoxy-1,2,3,4-tetrahydro-2-isoquinolinyl, 6,7-dihydroxy-1,2,3,4-tetrahydro-2-isoquinolinyl, 6,7-dimethoxy-1-methyl-1,2,3,4-tetrahydro-2-isoquinolinyl, 6,7-dihydroxy-1-methyl-1,2,3,4-tetrahydro-2-isoquinolinyl, 6-hydroxy-7-methoxy-1-methyl-1,2,3,4-tetrahydro-2-isoquinolinyl and the 1-(5-chloro-2-methylaminophenyl)-1,2,3,4-tetrahydro-2-isoquinolinyl radicals.

Salts of compounds of the formula I—depending on substitution—are all acid addition salts or all salts with bases. Particular mention may be made of the pharmacologically tolerable salts of the inorganic and organic acids and bases customarily used in pharmacy. Those suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluene-sulfonic acid, methanesulfonic acid or 3-hydroxy-2-naphthoic acid, where the acids are employed in the salt preparation—depending on whether a mono—or polybasic acid is concerned and depending on which salt is desired—in an equimolar quantitative ratio or one differing therefrom.

On the other hand, salts with bases are also suitable. Examples of salts with bases which may be mentioned are alkali metal salts (lithium, sodium, potassium) or calcium, aluminum, magnesium, titanium, ammonium, meglumine or guanidinium salts, where here, too, the bases are employed in the salt preparation in an equimolar quantitative ratio or one differing therefrom.

Pharmacologically intolerable salts which can initially be obtained as process products, for example, in the preparation of the compounds according to the invention on an industrial scale, are converted into pharmacologically tolerable salts by processes known to the person skilled in the art.

Like the abovementioned salts, the invention also relates to solvates of the compounds of the formula I. In this case particular mention may be made of the hydrates.

Compounds of the formula I to be emphasized are those in which

R1 is hydrogen or 1–4C-alkyl,

R2 is 1–7C-alkyl, phenyl, phenyl-1–4C-alkyl, Ar-1–4C-alkyl, Ar or 1–5C-alkylene substituted by —N(R7)R8, where Ar is phenyl substituted by R9, R10 and R11, R3 is phenyl substituted by R31 and R32, where R31 is hydrogen, hydroxyl, halogen, nitro, cyano, carboxyl, trifluoromethyl, amino or mono- or di-1–4C-alkylamino and R32 is hydrogen, hydroxyl, halogen, nitro or trifluoromethyl, R4 is 1–4C-alkyl, A is 4–13C-alkylene, R5 is Ar1 and R6 is Ar2, or in which R5 and R6 together are methylene substituted by Ar1 and Ar2[=C(Ar1)Ar2], or in which R5 is hydrogen and R6 is methyl substituted by Ar1 and Ar2[—CH(Ar1)Ar2] or hydroxymethyl substituted by Ar1 and Ar2 [—C(OH)(Ar1)Ar2] where Ar1 is phenyl or phenyl substituted by one or two identical or different substituents from the group consisting of hydroxyl, halogen, nitro and trifluoromethyl and Ar2 is phenyl or phenyl substituted by one or two identical or different substituents from the group consisting of hydroxyl and halogen, R7 is 1–4C-alkyl, phenyl-1–4C-alkyl or Ar-1–4C-alkyl and R8 is 1–4C-alkyl, phenyl-1–4C-alkyl or Ar-1–4C-alkyl, where Ar is phenyl substituted by R9, R10 and R11, or in which R7 and R8, together and including the nitrogen atom to which both are bonded, are an unsubstituted or substituted heterocycle which is selected from the group consisting of pyrrolidine, piperidine, piperazine, morpholine, indoline, 1,2,3,4-tetrahydroquinoline, 1,2,3,4-tetrahydroisoquinoline, decahydroquinoline and decahydroisoquinoline, where a substituted pyrrolidino radical is substituted by one or two identical or different substituents selected from the group consisting of 1–4C-alkyl, 1–4C-alkoxy, 1–4C-alkoxycarbonyl and carboxyl, a substituted piperidino radical is substituted by one, two or three identical or different substituents selected from the group consisting of 1–4C-alkyl, 1–4C-alkoxy, phenyl, phenyl substituted by R9, R10 and R11 and phenyl-1–4C-alkyl, a substituted piperazino radical in the 4- position is substituted by a substituent selected from the group consisting of 1–4C-alkyl, 1–4C-alkoxycarbonyl, phenyl, phenyl substituted by R9, R10 and R11, phenyl-1–4C-alkyl, phenyl-1–4C-alkyl substituted in the phenyl radical by R9, R10 and R11, and benzhydryl, a substituted morpholino radical having one or two identical or different 1–4C-alkyl radicals, a substituted 1,2,3,4-tetrahydroquinoline radical is substituted by one or two identical or different substituents selected from the group consisting of 1–4C-alkyl, 1–4C-alkoxycarbonyl and halogen, a substituted 1,2,3,4-tetrahydroisoquinoline radical can be substituted in the benzo moiety by one or two substituents selected from the group consisting of hydroxyl, 1–4C-alkoxy and di-1–4C-alkylamino, and where R9 is hydrogen, 1–4C-alkyl, 1–4C-alkoxy, 1–4C-alkoxycarbonyl, halogen, 1–4C-alkylamino or nitro, R10 is hydrogen, 1–4C-alkyl, 1–4C-alkoxy, halogen or nitro and R11 is hydrogen or trifluoromethyl, and their salts.

Compounds of the formula I to be particularly emphasized are those in which

R1 is hydrogen or 1–4C-alkyl,

R2 is 1–5C-alkyl, phenyl, phenyl-1–4C-alkyl, Ar-1–4C-alkyl, Ar or 1–4C-alkylene substituted by —N(R7)R8, where Ar is phenyl substituted by R9, R10 and R11, R3 is phenyl substituted by R31 and R32, where R31 is hydrogen, halogen, nitro, trifluoromethyl, amino or mono- or di-1–4C-alkylamino and R32 is hydrogen, halogen or nitro, R4 is 1–4C-alkyl, A is 4–13C-alkylene, R5 is Ar1 and R6 is Ar2, or in which R5 and R6 together are methylene substituted by Ar1 and Ar2[=C(Ar1)Ar2], where Ar1 is phenyl or phenyl substituted by one or two identical or different substituents from the group consisting of hydroxyl and halogen and Ar2 is phenyl or phenyl substituted by one or two identical or different substituents from the group consisting of hydroxyl and halogen, R7 is 1–4C-alkyl or benzyl and R8 is 1–4C-alkyl or benzyl, or in which R7 and R8, together and including the nitrogen atom to which both are bonded, are an unsubstituted or substituted heterocycle which is selected from the group consisting of pyrrolidine, piperidine, piperazine, morpholine, 1,2,3,4-tetrahydroquinoline and 1,2,3,4-tetrahydroisoquinoline, where a substituted piperidino radical is substituted by a substituent selected from the group consisting of 1–4C-alkyl, phenyl and benzyl, a substituted piperazino radical in the 4-position is substituted by a substituent selected from the group consisting of 1–4C-alkyl, phenyl, phenyl substituted by 1–4C-alkoxy, and benzyl, a substituted morpholino radical is substituted by one or two identical or different 1–4C-alkyl radicals, a substituted 1,2,3,4-tetrahydroisoquinoline radical can be substituted on the benzo moiety by one or two 1–4C-alkoxy radicals, and where R9 is hydrogen, 1–4C-alkyl or 1–4C-alkoxy, R10 is hydrogen, 1–4C-alkyl or 1–4C-alkoxy, and R11 is hydrogen or trifluoromethyl, and their salts.

Preferred compounds of the formula I are those in which

R1 is hydrogen or 1–4C-alkyl,

R2 is 1–5C-alkyl, phenyl, phenyl-1–4C-alkyl, Ar-1–4C-alkyl, Ar or 1–4C-alkylene substituted by —N(R7)R8, where Ar is phenyl substituted by R9, R10 and R11, R3 is phenyl substituted by R31 and R32, where R31 is hydrogen, halogen, nitro or trifluoromethyl, and R32 is hydrogen, halogen or nitro, R4 is 1–4C-alkyl, A is 4–13C-alkylene, R5 is Ar1 and R6 is Ar2, or in which R5 and R6 together are methylene substituted by Ar1 and Ar2[=C(Ar1)Ar2], where Ar1 is phenyl or phenyl substituted by one or two identical or different substituents from the group consisting of hydroxyl and halogen and Ar2 is phenyl or phenyl substituted by one or two identical or different substituents from the group consisting of hydroxyl and halogen, R7 and R8, together and including the nitrogen atom to which both are bonded, are an unsubstituted or substituted heterocycle which is selected from the group consisting of pyrrolidine, piperidine, piperazine and morpholine, where the substituted piperazino radical in the 4-position is substituted by a 1–4C-alkyl radical, and where R9 is hydrogen, 1–4C-alkyl or 1–4C-alkoxy, R10 is hydrogen, 1–4C-alkyl or 1–4C-alkoxy, and R11 is hydrogen or trifluoromethyl, and their salts.

Particularly preferred compounds of the formula I are those in which

R1 is hydrogen or 1–4C-alkyl,

R2 is 1–5C-alkyl, phenyl, benzyl, Ar or 1–4C-alkylene substituted by —N(R7)R8, where Ar is phenyl substituted by R9, R3 is 3-nitrophenyl, R4 is 1–4C-alkyl, A is 4–10C-alkylene, R5 and R6 are phenyl, R7 and R8, together and including the nitrogen atom to which both are bonded, are a heterocycle which is selected from the group consisting of pyrrolidine, piperidine, morpholine and piperazine substituted by 1–4C-alkyl in the 4-position, R9 is 1–4C-alkoxy, and their salts.

The invention further relates to a process for the preparation of the compounds of the formula I (see attached formula sheet), in which R1, R2, R3, R4, A, R5 and R6 have the meanings indicated above, and their salts.

The process comprises reacting compounds of the formula II (see attached formula sheet), in which R1, R3, R4, A, R5 and R6 have the meanings indicated above and Y and Z are expediently 1–4C-alkoxy (preferably ethoxy), with amines $H_2N$—R2, in which R2 has the meanings indicated above, and/or if desired then converting compounds obtained into the salts and/or if desired then converting the salts obtained into the free compounds.

The reaction of compounds of the formula II with the amines $H_2N$—R2 is carried out by using methods known to the person skilled in the art (e.g. in the manner described in the examples). The reaction in this case is preferably conducted in suitable, preferably polar, aprotic solvents (such as dioxane and dimethylformamide), if desired with exclusion of water, under a nitrogen atmosphere and/or with addition of a catalytic amount of acid, preferably 4-toluenesulfonic acid. The reaction temperature is expediently between 0° C. and 160° C., but preferably at the boiling temperature of the solvent used, with reaction times of between 0.5 and 20 h, preferably between 4 and 10 h.

The amines of the formula $H_2N$—R2 are either known or can be prepared in a known manner.

The compounds of the formula II in which R1, R3, R4, A, R5, R6, Y and Z have the meanings indicated above are obtained by reaction of compounds of formula III (see attached formula sheet) in which R3, R4, A, R5, R6 and Z have the meanings indicated above, with orthoesters R1-C(Y)$_3$, in which R1 and Y have the meanings indicated above.

The reaction is carried out in a manner known per se to the person skilled in the art in suitable solvents, preferably using the orthoester R1-C(Y)$_3$ as a solvent and, if desired, under a nitrogen atmosphere (e.g. in the manner described in the examples).

In the abovementioned reaction, the starting compounds can be employed as such or optionally as their salts.

The orthoesters R1-C(Y)$_3$ are either known or can be prepared in a known manner.

The compounds of the formula III are obtained by reaction of compounds of formula IV (see attached formula sheet), in which R3, R4, Z and A have the meanings indicated above and X is a suitable leaving group, with compounds of the formula VII (see attached formula sheet), in which R5 and R6 have the meanings indicated above.

The reaction of the compounds IV and VII to III is carried out in a manner such as is known for the preparation of tertiary amines. Depending on the type of leaving group X, which is preferably a halogen atom, in particular a chlorine or bromine atom, the reaction can be carried out, if desired, in the presence of a base (e.g. of an inorganic carbonate, such as potassium carbonate) and/or with employment of an excess of amine VII. The conduct of the reaction can be favored by addition of alkali metal iodide. The reaction of the compounds IV and VII is otherwise carried out in a manner such as is known per se to the person skilled in the art and such as is described, for example, in the European patent Applications EP-A-242 829 or EP-A-314 038. The starting compounds can be employed here as such or, as preferred for compounds of the formula VII, in the form of their salts.

The compounds of the formula IV, in which R3, R4, Z and A have the abovementioned meanings and X is a leaving group, are likewise obtained in a manner known per se by oxidation of the corresponding compounds of the formula V (see attached formula sheet), in which R3, R4, Z and A have the abovementioned meanings and X is a leaving group.

The oxidation is carried out in a manner familiar to a person skilled in the art in inert solvents, such as, for example, dichloromethane, at temperatures between 0° and 200° C., preferably between 0° and 50° C.

Possible inorganic and organic oxidants for the oxidation (dehydrogenation) are those such as, for example, manganese dioxide, nitric acid, chromium(VI) oxide, sulfur, cerium(IV) ammonium nitrate, alkali metal dichromate, nitrogen oxides, chloranil, tetracyanobenzoquinone or anodic oxidation in the presence of a suitable electrolyte system.

The compounds of the formula V are obtained in a manner known per se by reaction of the compounds of the formula VI (see attached formula sheet), in which R3, R4, A and X have the abovementioned meanings, with amidinoacetic acid esters, such as, for example, with ethyl amidinoacetate hydrochloride. The reaction is carried out in a manner known per se to the person skilled in the art, e.g. in the manner described in the examples. The compounds of the formulae V, VI and VII are either known or they can be prepared in a manner known per se from corresponding starting compounds in an analogous manner. Thus the compounds VI are obtained, for example, by the reaction of diketones R4—COCH$_2$—CO—A—X with appropriate aldehydes R3—CHO.

The following examples serve to illustrate the invention in greater detail without restricting it. Likewise, further compounds of the formula I whose preparation is not described explicitly can be prepared in an analogous manner or in a manner familiar per se to the person skilled in the art using customary process techniques. In the examples, m.p. stands for melting point, h stands for hour(s), min stands for minute(s) and RT stands for room temperature. The invention preferably relates to the compounds mentioned in the examples and their salts and/or solvates.

EXAMPLES

Final Products 1. 3,4-Dihydro-2,7-dimethyl-3-[2-(4-morpholinyl)ethyl]-5-3-nitrophenyl)-4-oxo-6-[1-oxo-11-(4,4-diphenyl-1-piperidinyl)undecyl]-pyrido[2,3-d]pyrimidine dihydrochloride 2 g of ethyl 2-(1-ethoxyethyliden)amino-6-methyl-4-(3-nitrophenyl)-5-[1-oxo-11-(4,4-diphenyl-1-piperidinyl)undecyl}pyridine-3-carboxylate and 0.34 g of N-(2-aminoethyl)morpholine in 60 ml of abs. dioxane are stirred at 120° C. for 6 h under nitrogen. The solvent is distilled off in vacuo. The residue is chromatographed through a silica gel column using ethyl acetate/methanol/NH$_4$OH 90:8:2 as an eluent. The chromatographically pure fractions are combined and concentrated in vacuo. The residue is dissolved in dichloromethane, and the solution is washed with water, dried over sodium sulfate and filtered. The filtrate is treated with ethereal hydrochloric acid, concentrated and dried in a high vacuum. The residue is crystallized from isopropanol, filtered off with suction and dried in a high vacuum. 1.6 g of the title compound of m.p.172.5–175° C. (dec.) are obtained.

2. 3,4-Dihydro-2,7-dimethyl-5-(3-nitrophenyl)-4-oxo-3-phenyl-6-[1-oxo-11-(4,4-diphenyl-1-piperidinyl)undecyl] pyrido[2,3-d]pyrimidine hydrochloride 0.6 g of ethyl 2-(1-ethoxyethyliden)amino-6-methyl-4-(3-nitrophenyl)-5-[1-oxo-11-(4,4-diphenyl-1-piperidinyl) undecyl]pyridine-3-carboxylate and 0.15 g of aniline are dissolved in 10 ml of abs. dimethylformamide, treated with a small spatula tipful of 4-toluenesulfonic acid and stirred at 155° C. for 6 h under nitrogen. The solvent is distilled off in vacuo, the residue is dissolved in ethyl acetate, and the solution is washed with water and concentrated again. The residue is chromatographed through a silica gel column using ethyl acetate/methanol/NH$_4$OH 90:8:2. The pure fractions are combined and concentrated, and the residue is dissolved in dichloromethane. The solution is extracted by shaking with water, dried over sodium sulfate and filtered. The filtrate is treated with ethereal ethyl acetate and concentrated. The residue is dried in a high vacuum, then triturated with ethyl acetate, and the solid obtained is filtered off with suction and dried. 0.1 g of the title compound of m.p. 159–161° C. (dec.) is obtained.

Further compounds of the formula I in which R3 is 3-nitrophenyl, R4 is methyl, R5 and R6 are phenyl and R1, R2 and A have the meanings indicated in Table A can be prepared from the corresponding starting compounds analogously to Examples 1 and 2. Me in Table A stands for methyl, H for hydrogen and Et for ethyl.

TABLE A

| Ex No. | R1 | R2 | A | Salt/solvate | M.p. [° C.] |
|---|---|---|---|---|---|
| 3 | H | Propyl | (CH$_2$)$_7$ | xH$_2$O | 90(dec.) |
| 4 | H | Pentyl | (CH$_2$)$_7$ | x2H$_2$O | 160(dec.) |
| 5 | Me | 2-(4-Morpholinyl)ethyl | (CH$_2$)$_7$ | x2HCl | 187(dec.) |

TABLE A-continued

| Ex No. | R1 | R2 | A | Salt/ solvate | M.p. [° C.] |
|---|---|---|---|---|---|
| 6 | H | Butyl | $(CH_2)_{10}$ | xHCl | 197–198(dec.) |
| 7 | H | Propyl | $(CH_2)_{10}$ | xHCl | 216(dec.) |
| 8 | H | Pentyl | $(CH_2)_{10}$ | xHCl | 188–190(dec.) |
| 9 | H | Phenyl | $(CH_2)_{10}$ | xHCl | 160(dec.) |
| 10 | H | Benzyl | $(CH_2)_{10}$ | xHCl | 206(dec.) |
| 11 | H | 4-Methoxyphenyl | $(CH_2)_{10}$ | | 149–150(dec.) |
| 12 | H | 2-(4-Morpholinyl)ethyl | $(CH_2)_{10}$ | x2HCl | 173(dec.) |
| 13 | Me | Propyl | $(CH_2)_7$ | xHCl | 140(dec.) |
| 14 | Me | Pentyl | $(CH_2)_7$ | xHCl | 145(dec.) |
| 15 | Me | 3-(4-Morpholinyl)propyl | $(CH_2)_{10}$ | x2HCl | 156–157(dec.) |
| 16 | Me | 2-(1-Piperidinyl)ethyl | $(CH_2)_{10}$ | x2HCl | 140(dec.) |
| 17 | H | 3-(4-Morpholinyl)propyl | $(CH_2)_{10}$ | x2HCl | 156–159(dec.) |
| 18 | Me | 2-(1-Piperidinyl)ethyl | $(CH_2)_7$ | x2HCl | 193(dec.) |
| 19 | Me | Butyl | $(CH_2)_4$ | xHCl | 192–194(dec.) |
| 20 | Me | Butyl | $(CH_2)_7$ | xHCl | 127(dec.) |
| 21 | H | Butyl | $(CH_2)_7$ | xHCl | 142(dec.) |
| 22 | H | Benzyl | $(CH_2)_7$ | xHCl | 137(dec.) |
| 23 | Me | Benzyl | $(CH_2)_7$ | xHCl | 154–157(dec.) |
| 24 | H | Butyl | $(CH_2)_4$ | xHCl | 223–227(dec.) |
| 25 | H | Butyl | $(CH_2)_5$ | xHCl | 221(dec.) |
| 26 | H | Phenyl | $(CH_2)_4$ | $xH_2O$ | 169–170(dec.) |
| 27 | H | Phenyl | $(CH_2)_5$ | xHCl | 174(dec.) |
| 28 | H | Phenyl | $(CH_2)_7$ | xHCl | 145(dec.) |
| 29 | H | Benzyl | $(CH_2)_4$ | xHCl | 220–221(dec.) |
| 30 | H | Benzyl | $(CH_2)_5$ | xHCl | 177–180(dec.) |
| 31 | H | 4-Methoxyphenyl | $(CH_2)_4$ | $xH_2O$ | 176–178(dec.) |
| 32 | H | 4-Methoxyphenyl | $(CH_2)_7$ | $xH_2O$ | 170–173(dec.) |
| 33 | H | 2-(4-Morpholinyl)ethyl | $(CH_2)_4$ | x2HCl | 185(dec.) |
| 34 | H | 2-(4-Morpholinyl)ethyl | $(CH_2)_7$ | x2HCl | 160(dec.) |
| 35 | H | 3-(4-Morpholinyl)propyl | $(CH_2)_7$ | x2HCl | 173–175(dec.) |
| 36 | H | 2-(1-Pyrrolidinyl)ethyl | $(CH_2)_7$ | x2HCl | 175(dec.) |
| 37 | H | 2-(1-Piperidinyl)ethyl | $(CH_2)_7$ | x2HCl | 176(dec.) |
| 38 | H | 3-(1-Piperidinyl)propyl | $(CH_2)_7$ | x2HCl | 165–168(dec.) |
| 39 | H | 3-(1-Pyrrolidinyl)propyl | $(CH_2)_7$ | x2HCl | 165(dec.) |
| 40 | Me | Butyl | $(CH_2)_5$ | xHCl | 157(dec.) |
| 41 | Me | Phenyl | $(CH_2)_7$ | xHCl | 174–177(dec.) |
| 42 | Me | Benzyl | $(CH_2)_5$ | xHCl | 171(dec.) |
| 43 | Me | 4-Methoxyphenyl | $(CH_2)_7$ | xHCl | 175(dec.) |
| 44 | Me | 3-(4-Morpholinyl)propyl | $(CH_2)_7$ | x2HCl | 175(dec.) |
| 45 | Me | 2-(1-Pyrrolidinyl)ethyl | $(CH_2)_7$ | x2HCl | 174–177(dec.) |
| 46 | Me | 3-(1-Piperidinyl)propyl | $(CH_2)_7$ | x2HCl | 175(dec.) |
| 47 | Me | 3-(4-Methylpiperazine-1-yl)propyl | $(CH_2)_7$ | x3HCl | 190(dec.) |
| 48 | Et | Butyl | $(CH_2)_4$ | xHCl | 220–222(dec.) |

Starting Compounds

A1. Ethyl 2-(1-ethoxyethyliden)amino-6-methyl-4-(3-nitrophenyl)-5-[1-oxo-11-(4,4-diphenyl-1-piperidinyl)undecyl]pyridine-3-carboxylate 5.7 g of ethyl 2-amino-6-methyl-4-(3-nitrophenyl)-5-[1-oxo-11-(4,4-diphenyl-1-piperidinyl)undecyl]pyridine-3-carboxylate hydrochloride and 150 ml of triethyl orthoacetate are heated at 125° C. for 72 h with passage of nitrogen. The solution is concentrated in vacuo, and the residue is dried and then chromatographed through a silica gel column using petroleum ether/ethyl acetate/triethylamine 7:3:0.5 as eluent. The pure fractions are combined and concentrated, and the residue is dried in a high vacuum. 3 g of the title compound are obtained as a pale yellow oil.

B1. Ethyl 2-amino-6-methyl4-(3-nitrophenyl)-5-[1-oxo-11-(4,4-diphenyl-1-piperidinyl)undecyl]pyridine-3-hydrochloride 8.35 g of ethyl 2-amino-6-methyl-4-(3-nitrophenyl)-5-(11-bromo-1-oxo-undecyl)pyridine-3-carboxylate, 4.53 g of 4,4-diphenylpiperidine hydroacetate, 0.37 g of sodium iodide, 3.55 g of sodium carbonate and 10 drops of triethylamine are heated to boiling under reflux for 20 h in 150 ml of methyl isobutyl ketone. After cooling, the mixture is washed once with water and twice with satd. sodium chloride solution, dried over sodium sulfate, filtered and concentrated. The residue is chromatographed through a silica gel column using petroleum ether/ethyl acetate/triethylamine 7:3:0.5 as an eluent. The pure fractions are combined and concentrated, and the residue is dissolved in dichloromethane. The solution is treated with ethereal hydrochloric acid and concentrated. After redistilling twice with dichloromethane, the residue is dried in vacuo. 8.7 g of the title compound are obtained as a solid foam.

C1. Ethyl 2-amino-6-methyl-4-(3-nitrophenyl)-5-(11-bromo-1-oxo-undecyl)pyridine-3-carboxylate 41.9 g of ethyl 2-amino-1,4-dihydro-6-methyl-4-(3-nitrophenyl)-5-(11-bromo-1-oxo-undecyl)pyridine-3-carboxylate are dissolved in 300 ml of dichloromethane and 137 g of manganese dioxide are added. The mixture is stirred at RT for 20 h, then filtered off through Celite and the filtrate is washed with water. The oil remaining after concentration of the filtrate crystallizes on standing or is seeded. It is triturated with diisopropyl ether and filtered off with suction. 23.2 g of the title compound of m.p. 73–74° C. are obtained.

D1. Ethyl 2-amino-1,4-dihydro-6-methyl-4-(3-nitrophenyl)-5-(11-bromo-1-oxo-undecyl)pyridine-3-carboxylate 12.7 g of ethyl amidinoacetate hydrochloride and 33.4 g of 14-bromo-3-(3-nitrobenzylidene)tetradecane-2,4-dione are dissolved in 300 ml of ethanol and the solution is treated with 14.5 ml of a 5.25M of sodium methoxide solution. The mixture is heated to boiling under reflux for 7 h and then concentrated in vacuo. The residue is dissolved in ethyl acetate and the solution is washed with water, dried over sodium sulfate, filtered and concentrated again. The oily residue is dried in vacuo and reacted in the next stage without further purification.

E1. 14-Bromo-3-(3-nitrobenzylidene)-tetradecane-2,4-dione 4.7 g of 3-nitrobenzaldehyde and 9.5 g of 14-bromotetradecane-2-4-dione are dissolved in 100 ml isopropanol, 0.18 ml of acetic acid and 0.15 ml of piperidine are added and the mixture is stirred at RT for 4.5 days. It is cooled in an ice bath, and the crystallized product is filtered off with suction, washed with ice-cold isopropanol and dried. 10.5 g of the compound of m.p. 64–67° C. are obtained.

Commercial Utility

The compounds of the formula I and their salts have useful properties which make them commercially utilizable. They improve the action of antibiotics and/or cytostatics in a synergistic manner, and they are moreover able to overcome resistance to antibiotics and/or cytostatics which is already present or occurs in the course of therapy. They can be employed here not only in combination with other cytostatics or antibiotics for overcoming so-called drug resistance or multidrug resistance. Rather, they are suitable on account of their antineoplastic properties per se for the treatment of oncoses, for example for reducing or preventing metastasis formation and tumor growth in mammals, and on account of their antiproliferative properties, for example, for the treatment of dermatoses.

In their outstanding efficacy, which is seen in a marked overcoming of resistance and which is coupled with low toxicity, good bioavailability and the absence of undesirable side effects, compounds of the formula I and their salts differ in a surprising and advantageous manner from known resistance modulators and cancer chemotherapeutics.

The outstanding efficacy of compounds of the formula I and their salts permits their use in human medicine as sole or concomitant chemotherapeutics for the treatment of tumors, e.g. leukemia, ovarian carcinomas, testicular tumors, prostate carcinomas, bladder tumors, kidney tumors, esophageal carcinomas and other malignant tissue neoplasms, in particular of bowel cancer, breast cancer, bronchial carcinomas and lung carcinomas. In a manner identical to that in which the compounds according to the invention can overcome the drug resistance of tumor cells, the resistance to certain antimalarial agents, such as, for example, chloroquine, can be eliminated by the compounds according to the invention. In the case of the overcoming of the resistance to antibiotics, the overcoming of the resistance to chloroquine is therefore of particular importance, as the increasing development of resistance in some parts of the world of Plasmodium falciparum (the causative organism of tropical malaria) to this proven antimalarial agent causes increasing difficulties in controlling malaria. The compounds according to the invention are furthermore suitable not only for overcoming resistance to antibiotics. Rather, on account of their antiparasitic properties, they can be employed for the treatment of parasitic disorders, in particular tropical parasitic disorders such as, for example, malaria, sleeping sickness, filariasis, or onchocerciasis.

In the improvement of the action or the overcoming of the development of resistance to cytostatics, it is of particular importance that the dose of the cytostatic administered can be reduced, which leads to a clear reduction of the toxic side effects, and that the number of employable cytostatics is increased, so that specifically the cytostatic optimally suitable for the intended tumor and the intended patient can be selected.

In this connection, it should also be pointed out that on account of the small effect of the compounds of the formula I on the cardiovascular system, e.g. on the blood pressure and the heart rate, these compounds can be administered in therapeutically efficacious doses without the danger of undesirable side effects on the cardiovascular system.

If the compounds of the formula I and/or their pharmacologically tolerable salts are administered as resistance modulators in antibiotic and cytostatic therapy, the compounds of the formula I can be administered together with the antibiotics or cytostatics in a fixed dose in the form of combination preparations, or the compounds of the formula I can be employed separately in any desired dose and a suitable administration form as associated and supportive active compounds in antibiotic or cytostatic therapy.

The ratio of compounds of the formula I to antibiotic or cytostatic depends on the disease to be treated, the diseased state of the patient and the antibiotic or cytostatic used. In this context, in general it has proven advantageous to administer the compounds of the formula I in the case of oral administration in a daily dose of approximately 0.5 to 30 mg/kg of body weight, in the case of intravenous administration in a daily dose of approximately 0.1 to 10 mg/kg of body weight, if desired in the form of several individual doses or as a continuous infusion, to achieve the desired result. The antibiotics or cytostatics are administered in the doses customary for them, but preferably in lower doses.

The invention additionally relates to the compounds of the formula I and their pharmacologically tolerable salts for use in the treatment of oncoses.

The invention likewise comprises the use of compounds of the formula I and their pharmacologically tolerable salts in the production of medicaments which are employed for the control of oncoses.

The invention furthermore relates to the use of compounds of the formula I in combination with antibiotics or cytostatics in antibiotic and/or cytostatic therapy.

The invention additionally relates to the use of compounds of the formula I for the production of medicaments which are to be employed in antibiotic and/or cytostatic therapy in combination with antibiotics or cytostatics.

The invention further relates to medicaments which contain one or more compounds of the general formula I and/or their pharmacologically tolerable salts.

The medicaments are prepared by processes known per se which are familiar to the person skilled in the art. As medicaments, the pharmacologically active compounds of the formula I and their salts (=active compounds) are employed either as such, or preferably in combination with suitable pharmaceutical auxiliaries in the form of tablets, coated tablets, capsules, suppositories, patches (for transdermal pharmaceutical administration), emulsions, suspensions, aerosols, sprays, ointments, creams, gels or solutions, the active compound content advantageously being between 0.1 and 95%.

The person skilled in the art is familiar on the basis of his expert knowledge with the auxiliaries which are suitable for the desired pharmaceutical formulations. Apart from solvents, gel-forming agents, suppository bases, tablet auxiliaries and other active compound excipients, it is possible to use, for example, antioxidants, dispersants, emulsifiers, antifoams, flavor corrigents, preservatives, solubilizers, colorants or, in particular, permeation promoters and complexing agents (e.g. cyclodextrins).

The active compounds can be administered rectally, by inhalation, parenterally (perlingually, intravenously, percutaneously) or orally.

Pharmacology

The ability of compounds of the formula I to overcome the resistance of tumor cells to cytostatics was demonstrated in various tests.

1. Measurements of the overcoming of the resistance to chemotherapeutics The overcoming of the resistance was measured on the human T-lymphoblastoid cell line CCRF-CEM and resistant lines derived therefrom (Niethammer et al., Advances in enzyme regulation, Weber G. (ed.) 29, 231–245, Pergamon Press: Oxford, New York, 1989) in a 3-day MTT test.

With the aid of the tetrazolium salt MTT (3-(4,5)-dimethylthiazol-2-yl)-2,5-diphenyltetrazolium bromide), the activity of cells can be determined via mitochondrial succinate dehydrogenase by the reduction of the tetrazolium salt to the blue formazan (Mosmann, Br. J. Cancer, 52: 205–214, 1983). The respective cell counts can then be inferred by means of the metabolic activity.

For screening, exponentially growing cultures were inoculated into 96-well microtiter plates (flat bottom) after Trypan Blue counting. The optimal inoculation density for each cell line was determined in growth experiments performed beforehand in order to guarantee exponential growth during the 3-day incubation.

Cells were plated out in 80 µl of medium (RPMI 1640, 50% human serum) with the aid of an automatic pipette (Electrapette, Tecnomara). The modulators to be investigated were dissolved in 100% DMSO and then further diluted with medium. The DMSO final concentration in all batches was 0.1%. 10 µl of cytostatic solution and 10 µl of modulator solution were added to the cell culture. In the case of the control, 20 µl of medium were correspondingly pipetted.

After a 3-day incubation in an incubator at 37° C. and 5% $CO_2$ atmosphere, 10 µl of MTT (final concentration 0.5 mg/ml) were pipetted. The plates-were then incubated for a further 4 h. After centrifugation at 200×g for 5 min (Labofuge 6000, Heraeus), 60 μl of the supernatant were removed and 150 μl of DMSO were added. The plates were shaken for 1 h on a microtiter plate shaker (Vibrax VXR, Ika) to solubilize the formazan formed.

The formazan formed was quantified with the aid of an automatic microtiter plate reader (EL 311, Bio-Tec Instruments) at 540 nm. The reference wavelength was 690 nm. The absorption data were given±SEM as mean values of a triplicate determination. Dose-response curves were obtained by plotting the formazan formation in percent of the control against the respective cytostatic concentration.

Table 1 which follows shows the investigation results determined. The cell line employed was in each case CCRF-VCR 1000, the cytostatic was vincristine. The concentration of the corresponding compounds was in each case 3 μM or 10 μM. The numbers of the investigated compounds correspond to the numbers in the examples. The investigation result given is the RMF value (Resistance Modulation Factor). The RMF value is the quotient of IC50 value (ng/ml) of cytostatic alone and IC50 value of cytostatic+ investigated compound.

TABLE 1

Determination of the resistance modulation factor

| Compound No.) | RMF value (in the presence of 50% human serum) |
|---|---|
| 1 (3 μM) | 256 |
| 1 (10 μM) | 686 |
| 2 (3 μM) | 12 |
| 2 (10 μM) | 357 |
| 3 (10 μM) | 325 |
| 4 (10 μM) | 128 |
| 5 (10 μM) | 804 |
| 6 (10 μM) | 813 |
| 7 (10 μM) | 530 |
| 8 (10 μM) | 333 |
| 9 (10 μM) | 304 |
| 10 (10 μM) | 353 |
| 11 (10 μM) | 240 |
| 12 (3 μM) | 119 |
| 12 (10 μM) | 648 |
| 13 (10 μM) | 1250 |
| 14 (10 μM) | 357 |
| 15 (10 μM) | 368 |
| 16 (10 μM) | 373 |
| 17 (10 μM) | 452 |
| 18 (10 μM) | 925 |
| 19 (10 μM) | 167 |
| 20 (10 μM) | 714 |
| 21 (10 μM) | 556 |
| 22 (10 μM) | 250 |
| 23 (10 μM) | 250 |

RMF value = IC50 (ng/ml) of cytostatic/IC50 (ng/ml) of cytostatic + respective compound.

2. Measurement of P-glycoprotein inhibition

Multidrug-resistant and -sensitive cells of the T-lymphoblastoid leukemia cell lines CCRF-VCR 1000 and CCRF-CEM are withdrawn from the cell culture and harvested by centrifugation. The cells are taken up in RPMI medium (pH=7.3) without fetal calf serum and incubated at 37° C. for 30 min with the rising concentrations of resistance modulators. Rhodamine 123 is then added (final concentration 0.8 mg/l) and the mixture is incubated at 37° C. for one further h. The cellular Rhodamine 123 fluorescence is measured with the aid of a fluorescence-activated cell sorter. The excitation wavelength is 488 nm. The Rhodamine 123 fluorescence is measured at 520 nm. From the data obtained, dose-response curves are plotted whose $EC_{50}$ value is used as a measure of the potency of a modulator for the elimination of the p-glycoprotein-mediated Rhodamine 123 diminished accumulation.

Table 2 which follows shows the $EC_{50}$ values determined for some investigated compounds. The number of the investigated compounds correspond to the numbers in the examples.

TABLE 2

Measurement of p-glycoprotein inhibition

| Compound No. | $pEC_{50}$ |
|---|---|
| 1 | 7.6 |
| 2 | 7.2 |
| 3 | 7.6 |
| 4 | 7.7 |
| 5 | 6.8 |
| 6 | 7.8 |
| 7 | 7.3 |
| 8 | 7.5 |
| 9 | 7.2 |
| 10 | 7.6 |
| 11 | 7.4 |
| 12 | 7.6 |
| 13 | 7.3 |
| 14 | 7.1 |
| 15 | 7.5 |
| 16 | 7.1 |
| 17 | 7.6 |
| 18 | 7.3 |
| 19 | 7.0 |
| 20 | 7.5 |
| 21 | 7.3 |
| 22 | 7.4 |
| 23 | 7.3 |

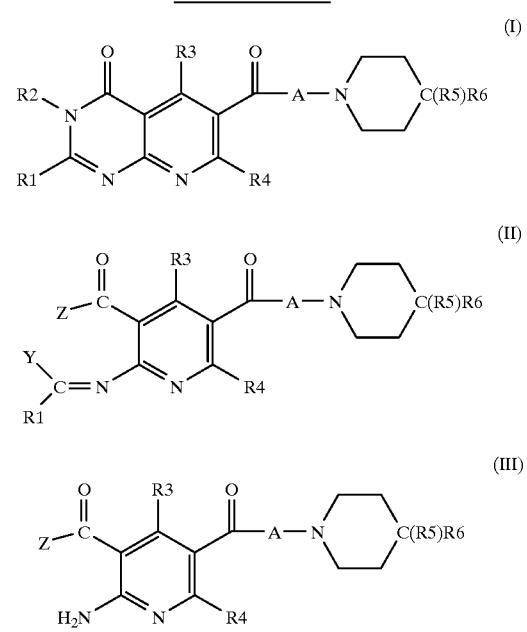

FORMULA SHEET

-continued

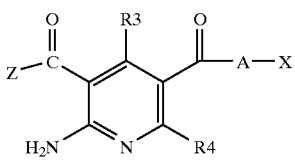
(IV)

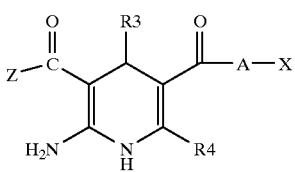
(V)

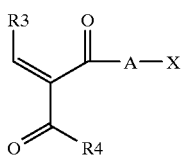
(VI)

(VII)

I claim:
1. A compound of the formula I

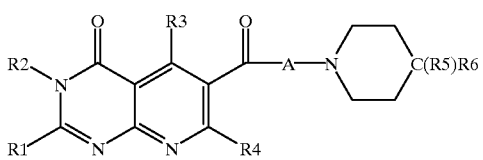
(I)

in which
R1 is hydrogen or 1–7C-alkyl,
R2 is 1–7C-alkyl, phenyl, phenyl-1–4C-alkyl, Ar-1–4C-alkyl, Ar or 1–7C-alkylene substituted by —N(R7)R8, where Ar is phenyl substituted by R9, R10 and R11,
R3 is phenyl or phenyl substituted by R31 and R32, where R31 is hydrogen, hydroxyl, halogen, nitro, cyano, carboxyl, trifluoromethyl, 1–4C-alkyl, 1–4C-alkoxy, completely or partly fluorine-substituted 1–4C-alkoxy, 1–4C-alkoxycarbonyl, 1–4C-alkylcarbonyl, amino or mono- or di-1–4C-alkylamino and R32 is hydrogen, hydroxyl, halogen, nitro, trifluoromethyl, 1–4C-alkyl or 1–4C-alkoxy,
R4 is 1–4C-alkyl,
A is 1–20C-alkylene or the group A1-X-A2, in which
A1 is 1–17C-alkylene,
X is O (oxygen) and
A2 is 2–18C-alkylene, where the total of the alkylene carbon atoms of A1 and A2 is not greater than 19,
R5 is Ar1 and
R6 is Ar2, or in which
R5 and R6 together are methylene substituted by Ar1 and Ar2 [=C(Ar1)Ar2], or in which R5 is hydrogen and
R6 is methyl substituted by Ar1 and Ar2 [—CH(Ar1)Ar2] or hydroxymethyl substituted by Ar1 and Ar2 [—C(OH)(Ar1)Ar2], where
Ar1 is phenyl or phenyl substituted by one or two identical or different substituents from the group consisting of hydroxyl, halogen, nitro, trifluoromethyl, 1–4C-alkyl and 1–4C-alkoxy and
Ar2 is phenyl or phenyl substituted by one or two identical or different substituents from the group consisting of hydroxyl, halogen, 1–4C-alkyl and 1–4C-alkoxy,
R7 is 1–7C-alkyl, 3–8C-cycloalkyl, phenyl-1–4C-alkyl or Ar-1–4C-alkyl and
R8 is 1–7C-alkyl, 3–8C-cycloalkyl, phenyl-1–4C-alkyl or Ar-1–4C-alkyl, where
Ar is phenyl substituted by R9, R10 and R11,
or in which
R7 and R8, together and including the nitrogen atom to which both are bonded, are an unsubstituted or substituted heterocycle which is selected from the group consisting of pyrrolidine, piperidine, piperazine, morpholine, thiomorpholine, indoline, octahydro-1H-indole, 1,2,3,4-tetrahydroquinoline, 1,2,3,4-tetrahydroisoquinoline, decahydroquinoline and decahydroisoquinoline, where
a substituted pyrrolidino radical is substituted by one or two identical or different substituents selected from the group consisting of 1–4C-alkyl, 1–4C-alkoxy, 1–4C-alkoxy-1–4C-alkyl, 1–4C-alkoxycarbonyl, 1–4C-alkylcarbonyloxy, hydroxy-1–4C-alkyl, hydroxyl and carboxyl,
a substituted piperidino radical is substituted by one, two or three identical or different substituents selected from the group consisting of 1–4C-alkyl, gem-di-1–4C-alkyl, 1–4C-alkoxy, 1–4C-alkoxy-1–4C-alkyl, 1–4C-alkoxycarbonyl, 1–4C-alkylcarbonyl, 1–4C-alkylcarbonyl-1–4C-alkyl, hydroxy-1–4C-alkyl, dihydroxy-1–4C-alkyl, di-1–4C-alkylamino, di-1–4C-alkylamino-1–4C-alkyl, pyrrolidino, piperidino, pyrrolidinyl-1–4C-alkyl, piperidinyl-1–4C-alkyl, carbamoyl, di-1–4C-alkylaminocarbonyl, piperidinocarbonyl, morpholinocarbonyl, phenyl, phenyl substituted by R9, R10 and R11, phenyl-1–4C-alkyl, benzoyl, benzoyl substituted by halogen, formyl, carboxyl, cyano, hydroxyl, halogen and sulfo,
a substituted piperazino radical in the 2-, 3-, 5- or 6-position can be substituted by a 1–4C-alkyl radical and in the 4-position is substituted by a substituent selected from the group consisting of 1–4C-alkyl, 3–7C-cycloalkyl, 3–7C-cycloalkyl-1–4C-alkyl, 1–4alkoxycarbonyl, 1–4C-alkoxycarbonyl-1–4C-alkyl, hydroxy-1–4C-alkyl, di-1–4C-alkylamino-1–4alkyl, halo-1–4C-alkyl, carbamoyl, phenyl, phenyl substituted by R9, R10 and R11, phenyl-1–4C-alkyl, phenyl-1–4C-alkyl substituted in the phenyl radical by R9, R10 and R11, naphthyl, benzhydryl and benzhydryl substituted by halogen,
a substituted morpholino radical is substituted by one or two identical or different 1–4C-alkyl radicals,
a substituted indolin-1-yl radical in the 2- and/or 3-position can be substituted by a carboxyl group or by one or two identical or different 1–4C-alkyl radicals, and can be substituted in the benzo moiety by one or two identical or different substituents selected from the group consisting of 1–4C-alkyl, halogen and nitro, a substituted 1,2,3,4-tetrahydroquinoline radical is substituted by one or two identical or different substituents selected from the group consisting of 1–4C-alkyl, 1–4C-alkoxycarbonyl and halogen, a substituted 1,2,3,4-tetrahydroisoquinoline radical can be substituted in the positions 1,3 and/or 4 by one or two identical or different substituents selected from the group consisting of 1–4C-alkyl, carboxyl, phenyl, phenyl substituted by R9, R10 and R11, phenyl-1–4C-alkyl and phenyl-1–4C-alkyl substituted in the phenyl radical by R9, R10 and R11, and can be substituted in the benzo moiety by one or two substituents selected from the group consisting of hydroxyl, 1–4C-alkoxy and di-1–4C-alkylamino, and where R9 is hydrogen, hydroxyl, 1–4C-alkyl, 1–4C-alkoxy, 1–4C-alkylcarbonyl, halogen, 1–4C-alkylamino or nitro, R10 is hydrogen, hydroxyl, 1–4C-alkyl, 1–4C-alkoxy, halogen or nitro and R11 is hydrogen or trifluoromethyl, or its salts.

2. A compound of the formula I as claimed in claim 1, in which

R1 is hydrogen or 1–4C-alkyl,

R2 is 1–7C-alkyl, phenyl, phenyl-1–4C-alkyl, Ar-1–4C-alkyl, Ar or 1–4C-alkylene substituted by —N(R7)R8, where Ar is phenyl substituted by R9, R10 and R11, R3 is phenyl substituted by R31 and R32, where R31 is hydrogen, hydroxyl, halogen, nitro, cyano, carboxyl, trifluoromethyl, amino or mono- or di-1–4C-alkylamino and R32 is hydrogen, hydroxyl, halogen, nitro or trifluoromethyl, R4 is 1–4C-alkyl, A is 4–13C-alkylene, R5 is Ar1 and R6 is Ar2, or in which R5 and R6 together are methylene substituted by Ar1 and Ar2 [=C(Ar1)Ar2], or in which R5 is hydrogen and R6 is methyl substituted by Ar1 and Ar2 [—CH(Ar1)Ar2] or hydroxymethyl substituted by Ar1 and Ar2 [—C(OH)(Ar1)Ar2] where Ar1 is phenyl or phenyl substituted by one or two identical or different substituents from the group consisting of hydroxyl, halogen, nitro and trifluoromethyl and Ar2 is phenyl or phenyl substituted by one or two identical or different substituents from the group consisting of hydroxyl and halogen, R7 is 1–4C-alkyl, phenyl-1–4C-alkyl or Ar-1–4C-alkyl and R8 is 1–4C-alkyl, phenyl-1–4C-alkyl or Ar-1–4C-alkyl, where Ar is phenyl substituted by R9, R10 and R11, or in which R7 and R8, together and including the nitrogen atom to which both are bonded, are an unsubstituted or substituted heterocycle which is selected from the group consisting of pyrrolidine, piperidine, piperazine, morpholine, indoline, 1,2,3,4-tetrahydroquinoline, 1,2,3,4-tetrahydroisoquinoline, decahydroquinoline and decahydroisoquinoline, where a substituted pyrrolidino radical is substituted by one or two identical or different substituents selected from the group consisting of 1–4C-alkyl, 1–4C-alkoxy, 1–4C-alkoxycarbonyl and carboxyl, a substituted piperidino radical is substituted by one, two or three identical or different substituents selected from the group consisting of 1–4C-alkyl, 1–4C-alkoxy, phenyl, phenyl substituted by R9, R10 and R11 and phenyl-1–4C-alkyl, a substituted piperazino radical in the 4-position is substituted by a substituent selected from the group consisting of 1–4C-alkyl, 1–4C-alkoxycarbonyl, phenyl, phenyl substituted by R9, R10 and R11, phenyl-1–4C-alkyl, phenyl-1–4C-alkyl substituted in the phenyl radical by R9, R10 and R11, and benzhydryl, a substituted morpholino radical having one or two identical or different 1–4C-alkyl radicals, a substituted 1,2,3,4-tetrahydroquinoline radical is substituted by one or two identical or different substituents selected from the group consisting of 1–4C-alkyl, 1–4C-alkoxycarbonyl and halogen, a substituted 1,2,3,4-tetrahydroisoquinoline radical can be substituted in the benzo moiety by one or two substituents selected from the group consisting of hydroxyl, 1–4C-alkoxy and di-1–4C-alkylamino, and where R9 is hydrogen, 1–4C-alkyl, 1–4C-alkoxy, 1–4C-alkoxycarbonyl, halogen, 1–4C-alkylamino or nitro, R10 is hydrogen, 1–4C-alkyl, 1–4C-alkoxy, halogen or nitro and R11 is hydrogen or trifluoromethyl, or its salts.

3. A compound of the formula I as claimed in claim 1, in which

R1 is hydrogen or 1–4C-alkyl,

R2 is 1–5C-alkyl, phenyl, phenyl-1–4C-alkyl, Ar-1–4C-alkyl, Ar or 1–4C-alkylene substituted by —N(R7)R8, where Ar is phenyl substituted by R9, R10 and R11, R3 is phenyl substituted by R31 and R32, where R31 is hydrogen, halogen, nitro, trifluoromethyl, amino or mono- or di-1–4C-alkylamino and R32 is hydrogen, halogen or nitro, R4 is 1–4C-alkyl, A is 4–13C-alkylene, R5 is Ar1 and R6 is Ar2, or in which R5 and R6 together are methylene substituted by Ar1 and Ar2 [=C(Ar1)Ar2], where Ar1 is phenyl or phenyl substituted by one or two identical or different substituents from the group consisting of hydroxyl and halogen and Ar2 is phenyl or phenyl substituted by one or two identical or different substituents from the group consisting of hydroxyl and halogen, R7 is 1–4C-alkyl or benzyl and R8 is 1–4C-alkyl or benzyl, or in which R7 and R8, together and including the nitrogen atom to which both are bonded, are an unsubstituted or substituted heterocycle which is selected from the group consisting of pyrrolidine, piperidine, piperazine, morpholine, 1,2,3,4-tetrahydroquinoline and 1,2,3,4-tetrahydroisoquinoline, where a substituted piperidino radical is substituted by a substituent selected from the group consisting of 1–4C-alkyl, phenyl and benzyl, a substituted piperazino radical in the 4-position is substituted by a substituent selected from the group consisting of 1–4C-alkyl, phenyl, phenyl substituted by 1–4C-alkoxy, and benzyl, a substituted morpholino radical is substituted by one or two identical or different 1–4C-alkyl radicals, a substituted 1,2,3,4-tetrahydroisoquinoline radical can be substituted on the benzo moiety ety by one or two 1–4C-alkoxy radicals, and where R9 is hydrogen, 1–4C-alkyl or 1–4C-alkoxy, R10 is hydrogen, 1–4C-alkyl or 1–4C-alkoxy, and R11 is hydrogen or trifluoromethyl, or its salts.

4. A compound of the formula I as claimed in claim 1, in which

R1 is hydrogen or 1–4C-alkyl,

R2 is 1–5C-alkyl, phenyl, phenyl-1–4C-alkyl, Ar-1–4C-alkyl, Ar or 1–4C-alkylene substituted by —N(R7)R8, where Ar is phenyl substituted by R9, R10 and R11, R3 is phenyl substituted by R31 and R32, where R31 is hydrogen, halogen, nitro or trifluoromethyl, and R32 is hydrogen, halogen or nitro, R4 is 1–4C-alkyl, A is 4–13C-alkylene, R5 is Ar1 and R6 is Ar2, or in which R5 and R6 together are methylene substituted by Ar1 and Ar2 [=C(Ar1)Ar2], where Ar1 is phenyl or phenyl substituted by one or two identical or different substituents from the group consisting of hydroxyl and halogen and Ar2 is phenyl or phenyl substituted by one or two identical or different substituents from the group consisting of hydroxyl and halogen, R7 and R8, together and including the nitrogen atom to which both are bonded, are an unsubstituted or substituted heterocycle which is selected from the group consisting of pyrrolidine, piperidine, piperazine and morpholine, where the substituted piperazino radical in the 4-position is substituted by a 1–4C-alkyl radical, and where R9 is hydrogen, 1–4C-alkyl or 1–4C-alkoxy, R10 is hydrogen, 1–4C-alkyl or 1–4C-alkoxy, and R11 is hydrogen or trifluoromethyl, or its salts.

5. A compound of the formula I as claimed in claim 1, in which

R1 is hydrogen or 1–4C-alkyl,

R2 is 1–5C-alkyl, phenyl, benzyl, Ar or 1–4C-alkylene substituted by —N(R7)R8, where Ar is phenyl substituted by R9, R3 is 3-nitrophenyl, R4 is 1–4C-alkyl, A is 4–10C-alkylene, R5 and R6 are phenyl, R7 and R8, together and including the nitrogen atom to which both are bonded, are a heterocycle which is selected from the group consisting of pyrrolidine, piperidine, morpholine and piperazine substituted by 1–4C-alkyl in the 4-position, R9 is 1–4C-alkoxy, or its salts.

6. A medicament comprising one or more compounds as claimed in claim 1 and/or their pharmacologically tolerable salts, together with customary pharmaceutical auxiliaries and/or excipients.

7. The use of compounds of the formula I as claimed in claim 1 and/or their pharmacologically tolerable salts for the production of medicaments for improving the action of antibiotics and/or cytostatics.

8. A medicament comprising one or more compounds as claimed in claim 1 and/or their pharmacologically tolerable salts in combination with cytostatics.

9. The use of compounds of the formula I as claimed in claim 1 and/or their pharmacologically tolerable salts for the production of medicaments for the treatment of oncoses.

* * * * *

UNITED STATES PATENT AND TRADEMARK OFFICE
CERTIFICATE OF CORRECTION

PATENT : 5,925,642

DATED : July 20, 1999

INVENTOR(S) : Ulrich

It is certified that error appears in the above-identified patent and that said Letters Patent is hereby corrected as shown below:

Column 21, line 21, delete "its salt" and insert --a salt thereof--

Column 22, line 32, delete "its salt" and insert --a salt thereof--

Column 23, line 15, delete "its salt" and insert --a salt thereof--

Column 24, line 6, delete "its salt" and insert --a salt thereof--

Column 24, line 26, delete "its salt" and insert --a salt thereof--

Column 24, line 27, insert "composition" before --comprising--

Column 24, line 28, after "and/or" delete "their" and insert --a--

Column 24, line 29, change "salts" to --salt--

Column 24, line 29, after "salts" insert --thereof--

Column 24, line 29, after "with" insert --a--

Column 24, line 29, change "auxiliaries" to --auxiliary--

Column 24, line 30, change "excipients" to --excipient--

UNITED STATES PATENT AND TRADEMARK OFFICE
CERTIFICATE OF CORRECTION

PATENT : 5,925,642

DATED : July 20, 1999

INVENTOR(S) : Ulrich

It is certified that error appears in the above-identified patent and that said Letters Patent is hereby corrected as shown below:

Replace claim 7 with:

In a method for improving the action of an antibiotic and/or cytostatic with which a susbject is being treated, the improvement which comprises administering to the subject an effective amount of a compound of formula I as claimed in claim 1 and/or a pharmocologically tolerable salt thereof.

Column 24, line 35, after "medicament" insert --composition--

Column 24, line 36, after "and/or" delete "their" and insert --a--

Column 24, line 37, delete "salts" and insert --salt--

Column 24, line 37, after "salts" insert --thereof--

Column 24, line 37, after "with" insert --a--

Column 24, line 37, change "cytostatics" to --cytostatic--

UNITED STATES PATENT AND TRADEMARK OFFICE
CERTIFICATE OF CORRECTION

PATENT : 5,925,642
DATED : July 20, 1999
INVENTOR(S): Ulrich

It is certified that error appears in the above-identified patent and that said Letters Patent is hereby corrected as shown below:

Replace claim 9 with:

A method for treating a subject afflicted with oncosis which comprises administering to the subject an effective amount of a compound of formula I as claimed in claim 1 and/or a pharmacologically tolerable salt thereof.

Signed and Sealed this

Twenty-third Day of November, 1999

Attest:

Attesting Officer

Q. TODD DICKINSON

Acting Commissioner of Patents and Trademarks